United States Patent

Seyed-Bolorforosh

[11] Patent Number: 5,841,889
[45] Date of Patent: Nov. 24, 1998

[54] ULTRASOUND IMAGE TEXTURE CONTROL USING ADAPTIVE SPECKLE CONTROL ALGORITHM

[75] Inventor: Mir Said Seyed-Bolorforosh, Brookfield, Wis.

[73] Assignee: General Electric Company, Milwaukee, Wis.

[21] Appl. No.: 581,668

[22] Filed: Dec. 29, 1995

[51] Int. Cl.$^6$ .................................................. G06K 9/00
[52] U.S. Cl. ........................ 382/128; 600/443; 600/448; 382/274
[58] Field of Search .................................... 382/128, 254, 382/274; 128/660.07, 661.08, 661.01; 600/443, 448, 463, 441

[56] References Cited

U.S. PATENT DOCUMENTS

| | | | |
|---|---|---|---|
| 5,291,525 | 3/1994 | Funderburk et al. | 357/345 |
| 5,482,044 | 1/1996 | Lin et al. | 128/660.07 |
| 5,522,392 | 6/1996 | Suorsa et al. | 128/661.08 |
| 5,568,813 | 10/1996 | Deitrich et al. | 128/661.01 |

OTHER PUBLICATIONS

Hokland, Jørn, et al., "Ultrasound Speckle Reduction Using Harmonic Oscillator Models", IEEE, 1994, pp. 215–224.

Primary Examiner—Jose L. Couso
Assistant Examiner—Matthew C. Bella
Attorney, Agent, or Firm—Dennis M. Flaherty; John H. Pilarski

[57] ABSTRACT

A method for controlling the contrast resolution and the tissue texture of ultrasonic images employs a signal processing algorithm to adjust an image by changing the tissue texture (speckle grain size). The algorithm increases the image contrast by allocating a different speckle pattern to different grey scale levels. This signal processing algorithm is based on the Hilbert transform. It uses the property of the Hilbert transform to generate a quadrature component of the given image which is modulated by the speckle pattern as well as all other image information. The quadrature component is then squared before being selectively added to or subtracted from the square of the in-phase component of the given image to control the information in the image. The added or subtracted signals have different textures (or spatial frequency components). The arithmetic operation between the in-phase and quadrature phase components determines the image texture. If this operation is done selectively, then the contrast and the texture of the image can be selectively controlled.

17 Claims, 12 Drawing Sheets

ULTRASOUND IMAGE TEXTURE CONTROL USING ADAPTIVE SPECKLE CONTROL ALGORITHM

FIELD OF THE INVENTION

This invention generally relates to ultrasound imaging, primarily clinical ultrasound images as well as industrial ultrasonic images. In particular, the invention relates to a method for controlling the contrast resolution and the tissue texture of ultrasonic images.

BACKGROUND OF THE INVENTION

Conventional ultrasound imaging systems comprise an array of ultrasonic transducers which are used to transmit an ultrasound beam and then receive the reflected beam from the object being studied. For ultrasound imaging, the array typically has a multiplicity of transducers arranged in a line and driven with separate voltages. By selecting the time delay (or phase) and amplitude of the applied voltages, the individual transducers can be controlled to produce a controlled beam of ultrasonic waves which combine to form a net ultrasonic wave that travels along a preferred vector direction and is focused at a selected point along the beam. Multiple firings may be used to acquire data representing the same anatomical information. The beam-forming parameters of each of the firing signals may be varied to provide a change in the position of focus or the beam profile of the received or transmitted wave-front for each firing, e.g., by transmitting successive beams along the same scan line with the focal point of each beam being shifted relative to the focal point of the previous beam. By changing the time delay and amplitude of the applied voltages, the beam with its focal point can be moved in a plane to scan the entire two-dimensional object plane.

The same principles apply when the transducer is employed to receive the reflected sound (receiver mode). The voltages produced at the receiving transducers are summed so that the net signal is indicative of the ultrasound waves reflected from a single focal point in the object. As with the transmission mode, this focused reception of the ultrasonic energy is achieved by imparting separate time delay (and/or phase shifts) and gains to the signal from each receiving transducer.

Such scanning comprises a series of measurements in which the steered ultrasonic wave is transmitted, the system switches to receive mode after a short time interval, and the reflected ultrasonic wave is received and stored. Typically, transmission and reception are steered in the same direction during each measurement to acquire data from a series of points along an acoustic beam or scan line. The receiver is dynamically focused at a succession of ranges along the scan line as the reflected ultrasonic waves are received.

Figure 1:
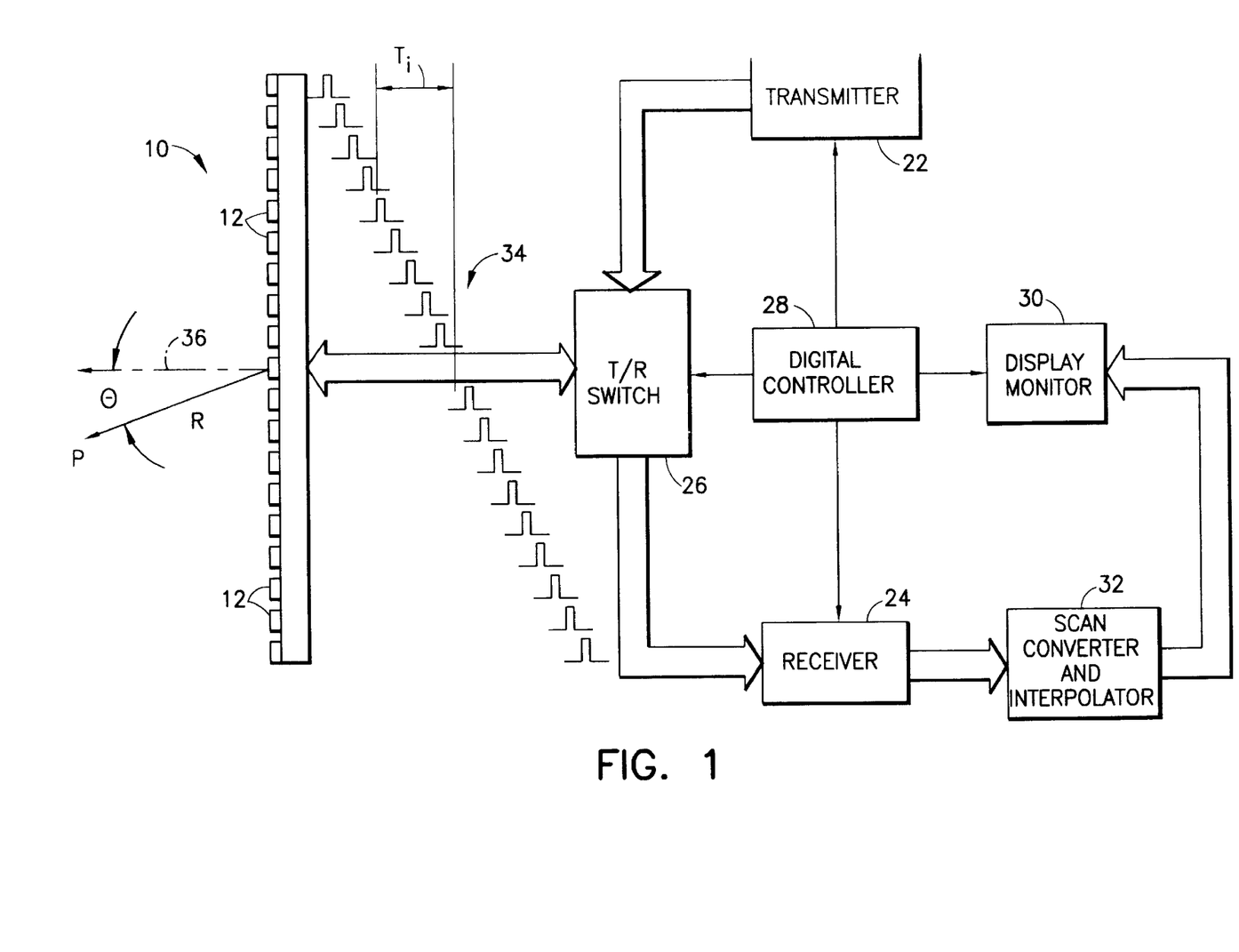
FIG. 1 is a block diagram showing the major functional subsystems within a real-time ultrasound imaging system.

Referring to FIG. 1, the ultrasonic imaging system incorporating the invention includes a transducer array 10 comprised of a plurality of separately driven transducer elements 12, each of which produces a burst of ultrasonic energy when energized by a pulsed waveform produced by a transmitter 22. The ultrasonic energy reflected back to transducer array 10 from the object under study is converted to an electrical signal by each receiving transducer element 12 and applied separately to a receiver 24 through a set of transmit/receive (T/R) switches 26. Transmitter 22, receiver 24 and switches 26 are operated under control of a digital controller 28 responsive to commands by a human operator. A complete scan is performed by acquiring a series of echoes in which switches 26 are set to their transmit position, transmitter 22 is gated ON momentarily to energize each transducer element 12, switches 26 are then set to their receive position, and the subsequent echo signals detected by each transducer element 12 are applied to receiver 24, which combines the separate echo signals from each transducer element to produce a single echo signal which is used to produce a line in an image on a display monitor 30.

Transmitter 22 drives transducer array 10 such that the ultrasonic energy produced is directed, or steered, in a beam. To accomplish this, transmitter 22 imparts a time delay $T_i$ to the respective pulsed waveforms 34 that are applied to successive transducer elements 12. By adjusting the time delays $T_i$ appropriately in a conventional manner, the ultrasonic beam can be directed away from axis 36 by an angle $\theta$ and/or focused at a fixed range R. A sector scan is performed by progressively changing the time delays $T_i$ in successive excitations. The angle $\theta$ is thus changed in increments to steer the transmitted beam in a succession of directions.

The echo signals produced by each burst of ultrasonic energy reflect from objects located at successive ranges along the ultrasonic beam. The echo signals are sensed separately by each transducer element 12 and a sample of the magnitude of the echo signal at a particular point in time represents the amount of reflection occurring at a specific range. Due to the differences in the propagation paths between a reflecting point P and each transducer element 12, however, these echo signals will not be detected simultaneously and their amplitudes will not be equal. Receiver 24 amplifies the separate echo signals, imparts the proper time delay to each, and sums them to provide a single echo signal which accurately indicates the total ultrasonic energy reflected from point P located at range R along the ultrasonic beam oriented at the angle $\theta$. Demodulation can occur either before or after the individual received signals are summed together.

Figure 2:
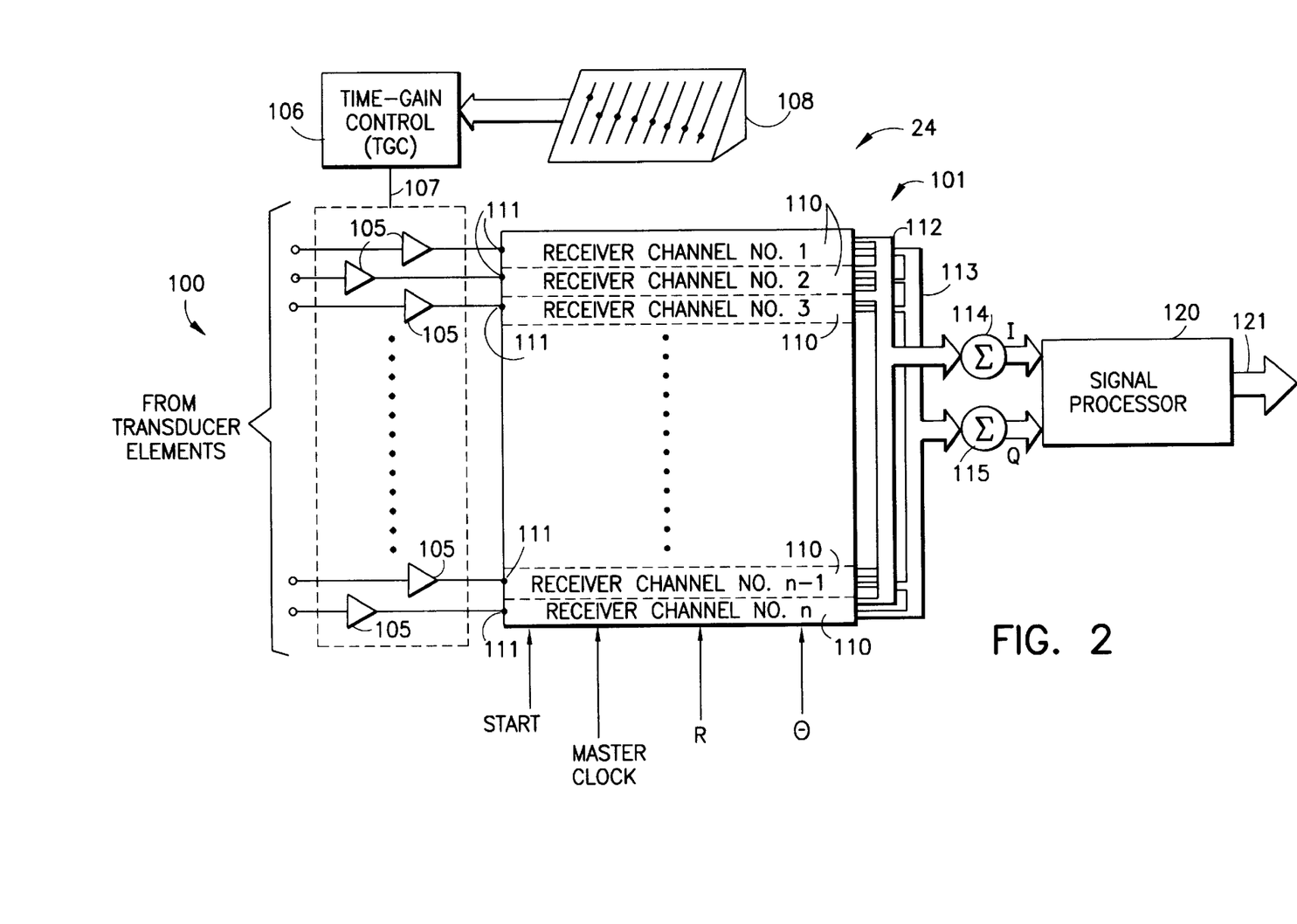
FIG. 2 is a block diagram of a receiver which forms part of the stem of FIG. 1.

To simultaneously sum the electrical signals produced by the echoes impinging on each transducer element 12, time delays are introduced into each separate transducer channel 110 of receiver 24 (see FIG. 2). The beam time delays for reception are the same delays ($T_i$) as the transmission delays described above. However, the time delay of each receiver channel is continuously changing during reception of the echo to provide dynamic focusing of the received beam at the range R from which the echo signal emanates.

Under the direction of digital controller 28, receiver 24 provides delays during the scan such that steering of receiver 24 tracks the direction $\theta$ of the beam steered by transmitter 22 and samples the echo signals at a succession of ranges R and provides the proper delays and phase shifts to dynamically focus at points P along the beam. Thus, each transmission of an ultrasonic pulse waveform results in the acquisition of a series of data points which represent the amount of reflected sound from a corresponding series of points P located along the ultrasonic beam.

Referring to FIG. 1, scan converter/interpolator 32 receives the series of data points produced by receiver 24 and converts the data into the desired image for display. In particular, the scan converter converts the acoustic image data from polar coordinate (R-$\theta$) sector format or Cartesian coordinate linear array to appropriately scaled Cartesian coordinate display pixel data at the video rate. This scan-converted acoustic data is then output for display on display monitor 30, which images the time-varying amplitude of the envelope of the signal as a grey scale.

Referring to FIG. 2, receiver 24 comprises three sections: a time-gain control section 100, a receive beamforming section 101 and a processor 102. Time-gain control (TGC) section 100 includes a respective amplifier 105 for each of the receiver channels 110 and a time-gain control circuit 106. The input of each amplifier 105 is connected to a respective one of transducer elements 12 to amplify the echo signal which it receives. The amount of amplification provided by amplifiers 105 is controlled through a control line 107 that is driven by TGC circuit 106, the latter being set by hand operation of potentiometers 108.

The receive beamforming section 101 of receiver 24 includes separate receiver channels 110. Each receiver channel 110 receives the analog echo signal from one of amplifiers 105 at an input 111. Each amplified signal is conveyed to a pair of quadrature detectors in the respective receiver channel, where the phases of the mixing reference frequency differ by 90°. Since this reference frequency is made identical to that of the transmitted pulses, the outputs from the low-pass filter in the receiver channel become the complex signals (I and Q) with phases that differ by 90°. These signals are output as a stream of digitized output values on an I bus 112 and a Q bus 113. Each of these I and Q baseband signals represents a demodulated sample of the echo signal envelope at a specific range R. These samples have been delayed such that when they are summed at summing points 114 and 115 with the I and Q samples from each of the other receiver channels 110, the summed signals indicate the magnitude and phase of the echo signal reflected from a point P located at range R on the steered beam ($\theta$). A signal processor 120 receives the beam samples from summing points 114 and 115 and produces an output 121 to scan converter 32 (see FIG. 1). Alternatively, the demodulation can be performed after the individual received signals are summed.

A typical ultrasound image obtained using an ultrasonic transducer exhibits a granular appearance which is caused by the coherent interference. This is known as the speckle. The speckle pattern in a given ultrasound image is a function of the beam profile of the scanning beam together with the scatterer size and distribution in the given image [see Powis et al., "A Thinker's Guide to Ultrasonic Imaging", Urban & Schwarzenberg, Baltimore/Munich (1984), p. 225]. Different tissue types have different speckle patterns. The speckle dot size (grain size), shape, separation repeated pattern (frequency) and amplitude all contribute to the image appearance. This information is used to distinguish between different tissue types in a given image. The presence of a number of small (compared to a wavelength) reflectors with uniform distribution in a given resolution cell (or three-dimensional point spread function) results in a variation in the magnitude of the detected signal. This is caused by the destructive and constructive interference of the signals at each transducer element. This variation in amplitude has a random appearance. This varies with position due to the constructive and destructive interference. This results in the speckle pattern in the ultrasound image. A typical computer simulation for modeling the speckle pattern in an ultrasound image was reported by Bamber et al. in "Ultrasonic B-Scanning: A Computer Simulation", Phys. Med. Biol., Vol. 25, No. 3, 463–479 (1980). The ability to distinguish between different tissue types in a clinical ultrasound image is very important for the detection of diseased tissue. The low contrast between different reflectors is a major challenge in an ultrasound image, as reported by Hall et al. in "Ultrasound Contrast-Detail Analysis: A Preliminary Study in Human Observer Performance," Medical Physic., Vol. 20, No. 1, Jan./Feb., 117–127 (1993), and by Wagner in "Low Contrast Sensitivity of Radiological, CT, Nuclear Medicine and Ultrasound Medical Imaging Systems," IEEE Trans. Med. Imag., Vol. MI-2, No. 3, Sep., 105–121 (1983). The proposed algorithm adaptively controls the speckle grain characteristic in order to improve the distinction between different tissue types.

SUMMARY OF THE INVENTION

The present invention controls the speckle pattern in an adaptive manner in order to improve the distinction between different tissue types with different reflection coefficients. It adaptively controls the speckle grain size and/or speckle pattern (peak and trough separation). This algorithm maintains the spatial information in the given image while improving the contrast resolution. The contrast resolution is the ability to differentiate between different tissue types or different reflectors.

The method of the invention controls the contrast resolution and the tissue texture of ultrasonic images, primarily clinical ultrasound images as well as industrial ultrasonic images. The signal processing algorithm of the invention allows the user to have a further degree of image control by adjusting the tissue texture in the given ultrasound image. This can be changed automatically in an adaptive fashion or controlled manually by the user. Hence not only the brightness of different tissue regions would vary but the tissue texture (speckle grain size) is also changed in order to increase the distinction between different regions. The processing can be considered as an extra control for the display of information for further enhancing and highlighting the different tissue regions. The algorithm increases the image contrast by allocating a different speckle pattern to different grey scale signal levels.

The signal processing algorithm of the invention can be used to improve the contrast resolution in a given ultrasound image and to increase the distinction between the backscattered or reflected signal from different tissue structures or different regions. This signal processing algorithm is based on the Hilbert transform. It uses the property of the Hilbert transform to generate a quadrature component of the given image signal which is modulated by the speckle pattern as well as all other image information. The quadrature component is then squared before being selectively added to or subtracted from the square of the in-phase component of the given image signal to control the information in the image. The added or subtracted signals have different textures (or spatial frequency components). The arithmetic operation between the in-phase and quadrature phase components determines the image texture. If this operation is done selectively, then the contrast and the texture of the image can be selectively modulated, which increases the distinction between the backscattered or reflected signals from regions with small difference in the backscatter or reflection coefficient. The reflectors causing the backscattered signal can be small diffuse specular reflectors such as the fatty globules in the tissue or large reflectors such as bone in the human body. This enhances the contrast resolution and the tissue texture differentiation in a given ultrasound image.

The advantage of using the Hilbert transform is the fact that the spatial image information of the original image is preserved. The proposed algorithm is intended to be performed on the two-dimensional image data. However, it can be performed in a one-dimensional manner as well.

The operation between the in-phase and quadrature phase components can be adjusted automatically based on the grey scale signal strength (backscattered signal strength) or it can be adjusted by the user. There is also a possibility of applying the operation in an adaptive fashion depending on the localized spatial frequency contents, the backscattered signal strength or both.

The algorithm of the invention controls the speckle "grain" size. Hence different tissue regions with different ultrasound backscatter coefficients can be coded by controlling their speckle grain size. This would help to distinguish between echoes from different tissue structures. The amount of variation or the profile of the change can be done in a number of different ways as required by the user, using the system settings or automatically in an adaptive manner.

DETAILED DESCRIPTION OF THE PREFERRED EMBODIMENTS

The algorithm for controlling the speckle "grain" size in accordance with the present invention is:

$$S_{out}(x,y) = |\{(Re(S_{in}(x,y))^2 + M(Im(S_{in}(x,y))^2\}|^{0.5} \quad (1)$$

where $S_{out}(x,y)$ is the two-dimensional output image after the adaptive speckle control operation; $S_{in}(x,y)$ is the input image; and Re and Im represent the in-phase (real) and quadrature (imaginary) phase components respectively of the input image. Here x is considered to be along the direction of propagation of ultrasound waves. The adaptive speckle control index is given by M, which is a controlled operator that determines the speckle characteristics within a range of values $-1 \leq M \leq 1$. The transformation of the proposed algorithm is determined by the localized value of the operator M over the given kernel size. That localized value is derived from an adaptive speckle control index map which stores index values as a function of the envelope-detected amplitude of the input image signal. This mapping can be linear or adaptive (nonlinear).

The in-phase and quadrature phase components of the given image are determined by the two-dimensional Hilbert transform of the input image signal. The Hilbert transform of a function f(x) is given by [Reference: Bracewell, "The Fourier Transform and Its Applications", 2nd Ed., McGraw-Hill (1978), p. 267]:

$$f_H(x) = \frac{1}{\pi} \int_{-\infty}^{\infty} \frac{f(x')}{(x'-x)} dx' \quad (2)$$

The transformed waveform is the quadrature component of the input waveform. All the spatial frequency components of the given input signal are preserved but the phase is rotated by $\pi/2$. As will be shown hereinbelow, the operation between the square sum of the in-phase and quadrature phase determines the shape of the waveform while preserving all the image information. The Hilbert transform can be applied in one or two dimensions to the input image. For a two-dimensional image $f(x,y)$, the Hilbert transforms along the x and y directions are given by:

$$f_{H,x}(x,y) = \frac{1}{\pi} \int_{-\infty}^{\infty} \frac{f(x',y)}{(x'-x)} dx' \quad (3a)$$

$$f_{H,y}(x,y) = \frac{1}{\pi} \int_{-\infty}^{\infty} \frac{f(x,y')}{(y'-y)} dy' \quad (3b)$$

The Hilbert transform of the input image is simply the quadrature component of the input image signal. The calculated two-dimensional Hilbert transform can then be used in Eq. (1) to control the speckle texture. Another parameter that is an input to Eq. (1) is the adaptive speckle control index M, which is obtained by first determining an adaptive speckle control index mapping input parameter P as follows:

$$P = \frac{1}{x_0 y_0} \int_{-x_0/2}^{x_0/2} \int_{-y_0/2}^{y_0/2} [(Re[S_{in}(x,y)])^2 + (Im[S_{in}(x,y)])^2]^{1/2} dx dy \quad (4)$$

where $x_0$ and $y_0$ are the width and height, respectively, of the kernel along the x and y directions. This kernel size determines the spatial resolution at which the algorithm is applied to the given input image. Ideally the kernel size should not be larger than a few times the correlation length of the given speckle pattern. A small kernel size ensures that the image texture information remains localized in each region. However, the minimum size of the kernel should be large enough to cover at least one speckle cell. The kernel size can be made adaptive so that the kernel size is larger when the mean signal level is low and vice versa. Alternatively, the kernel size can be adjusted depending on the spatial frequency contents of the given image. Hence the kernel size can be made smaller where the spatial frequency components are high and vice versa. Typically a good size for the kernel is two to four speckle cells.

The parameter P is input to a speckle control index mapping stored in a look-up table. The spackle control index mapping can be a linear or nonlinear function that maps P over the given kernel size into the corresponding value for M. It is also possible to have different $M_x$ and $M_y$ along the x and y directions respectively.

The mean square sum of the in-phase and quadrature phase components is equivalent to an envelope detection process. The envelope detected signal has wider speckle grain size due to the inherent nature of the envelope detection process. The reverse of this process is the mean square difference between the in-phase and quadrature phase components. The mean square difference makes the individual grains of the speckle pattern appear narrower. By selectively applying this operation, the speckle grain size can be controlled. For example the void (cyst) regions can be controlled to have a speckle pattern with very narrow grain size. Alternatively, the regions with high reflection intensity can be left with the speckle modulation information unaltered to improve the distinction between these two regions.

Alternatively, if there are two specular regions with different root mean square backscatter (or reflection) coefficients, then the region with the lower backscatter (or reflection) coefficient can be partially subtracted from its quadrature component while the second region can be left intact. This would have the effect of increasing the distinction between the two regions. If the amplitude difference between the two regions is small for the observer to distinguish between the two regions, then by selectively adding a small portion of the square of the quadrature component of the given image to one of the two regions (preferably the region with higher backscatter or reflection coefficient), an added degree of distinction between the two regions is introduced. This makes the task of distinction between two regions easier. The degree of addition between the two regions is determined by a mapping function which can be linear or nonlinear.

The speckle pattern can be modulated by addition or subtraction of the square of the in-phase and quadrature phase components as well as having intermediate stages of the addition and subtraction. The brightness of the speckle is unchanged but the speckle width is changed. This helps to further distinguish different tissue structures with different backscatter (or reflection) coefficients. The proposed algorithm can be selectively applied to the edges.

In order to show the effect of the speckle control algorithm in a typical grey scale image, consider a typical speckle pattern. In a simplified model, the signal from a typical speckle pattern can be represented by a series of sinusoidals with varying frequency over a given band of frequency determined by the correlation length (or bandwidth) of the speckle with varying amplitude (see FIG. 3A). In order to show the concept behind this idea, consider a one-dimensional model which shows the cross-sectional view of the speckle pattern. A typical speckle pattern was simulated by having a linear chirp waveform with varying amplitude which represents different regions with different backscatter (or reflection) coefficients. The actual image function which shows different backscatter regions appears as a solid line in FIG. 3A.

Figure 3A:
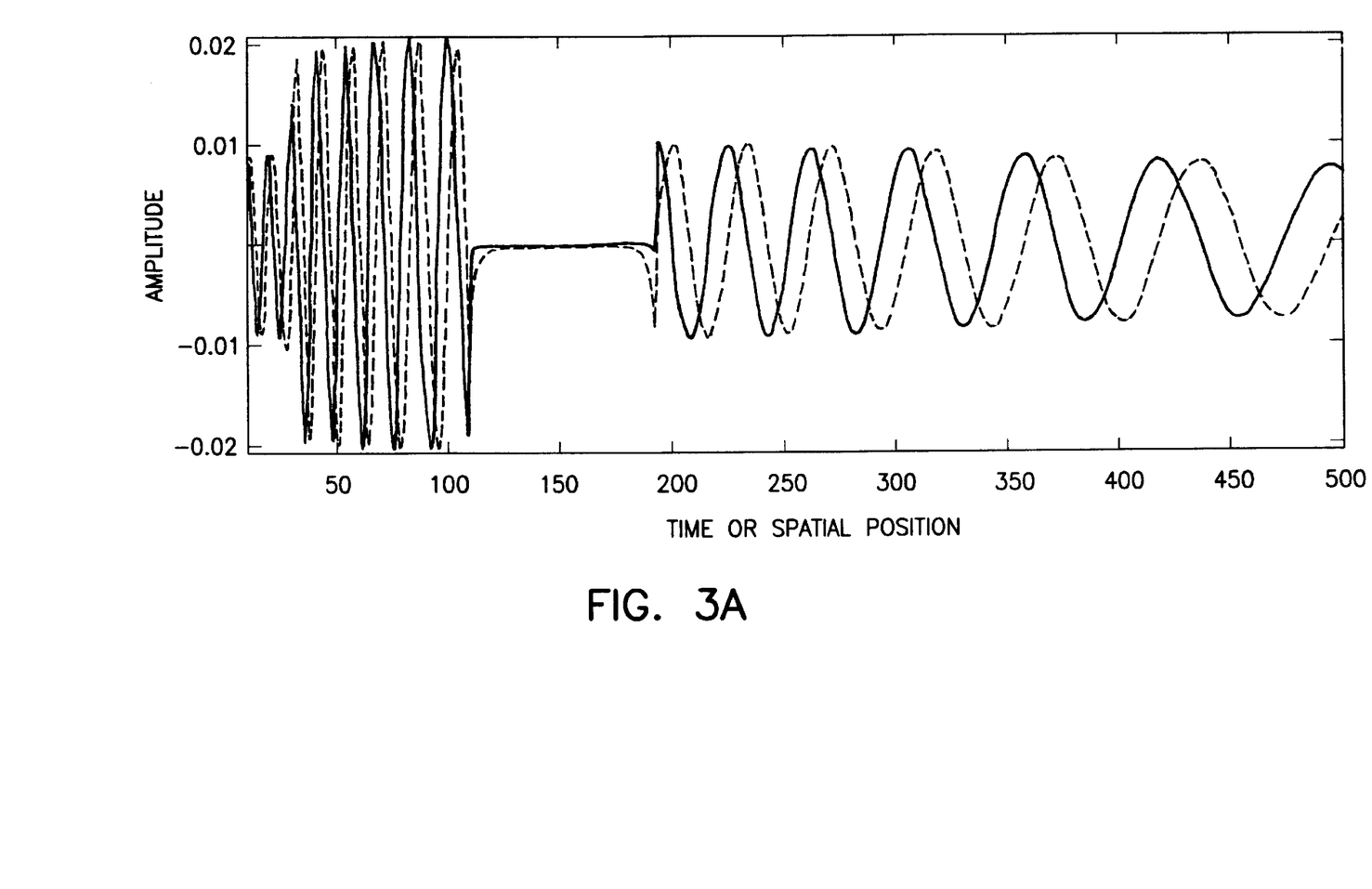
FIG. 3A is a graph of amplitude versus time for a simulated A-line signal (solid line) and the signal (dotted line) resulting from Hilbert transformation of that A-line signal.
Figure 3B:
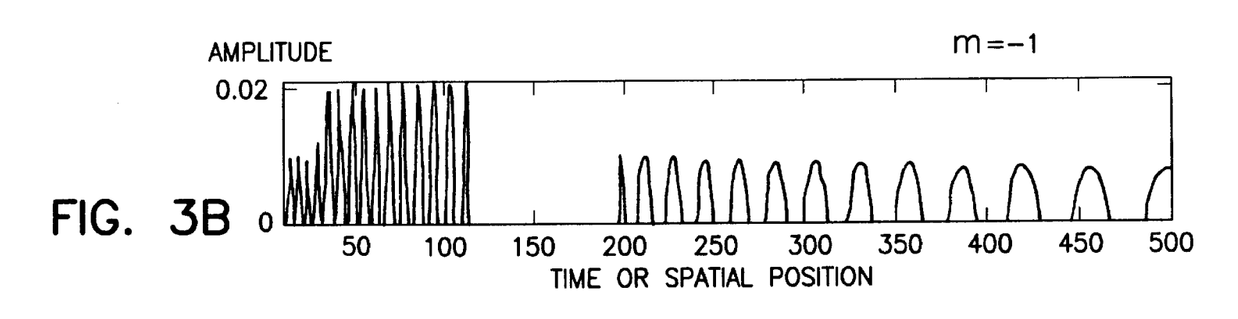
FIGS. 3B, 3C and 3D are graphs of amplitude versus time showing the signals resulting from transformation of the rectified A-line signal of FIG. 3A using the algorithm of the present invention with different transformation indices: $M=-1$ (FIG. 3B); $M=0$ (FIG. 3C); and $M=+1$ (FIG. 3D).
Figure 3C:
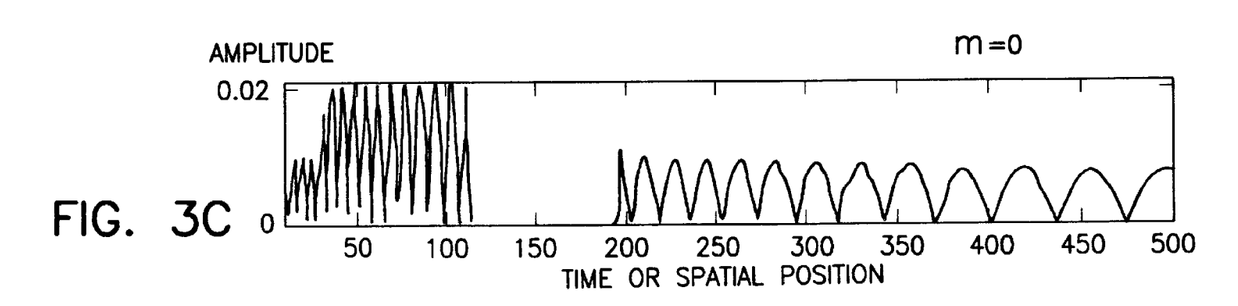
Figure 3D:
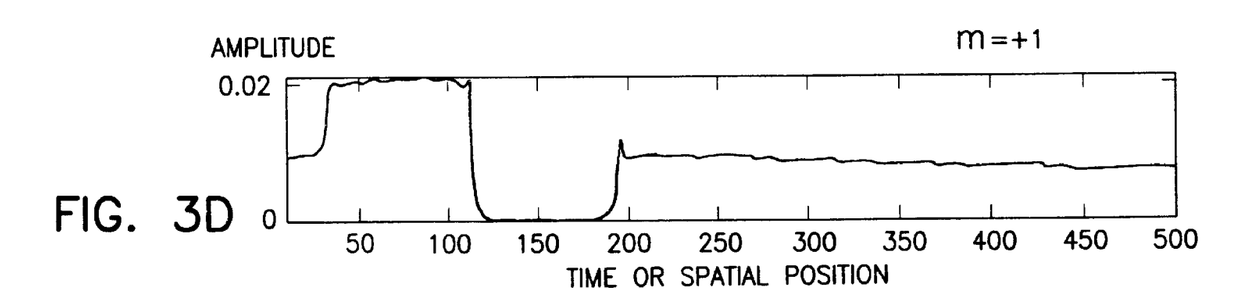

The solid line in FIG. 3A represents the waveform for a typical A-line signal. The Hilbert transform of this waveform (shown by the dotted line in FIG. 3A) is computed and then the three different operations are performed on the same data set. This represents the three different values for M. The three values shown in FIGS. 3B, 3C and 3D are −1, 0 and +1, respectively. The widths of the speckle grains are different for each value of M. By locally varying the index M, the width of the speckle grains is changed for different integrated backscattered (or integrated reflected) signal levels. The increase in the width for each speckle grain is a constant proportion of the original grain size. Also, after each of these operations the original image information is still preserved, showing the differences in the backscattered signal levels (or the differences in the reflected signal levels) from different regions.

Figure 4:
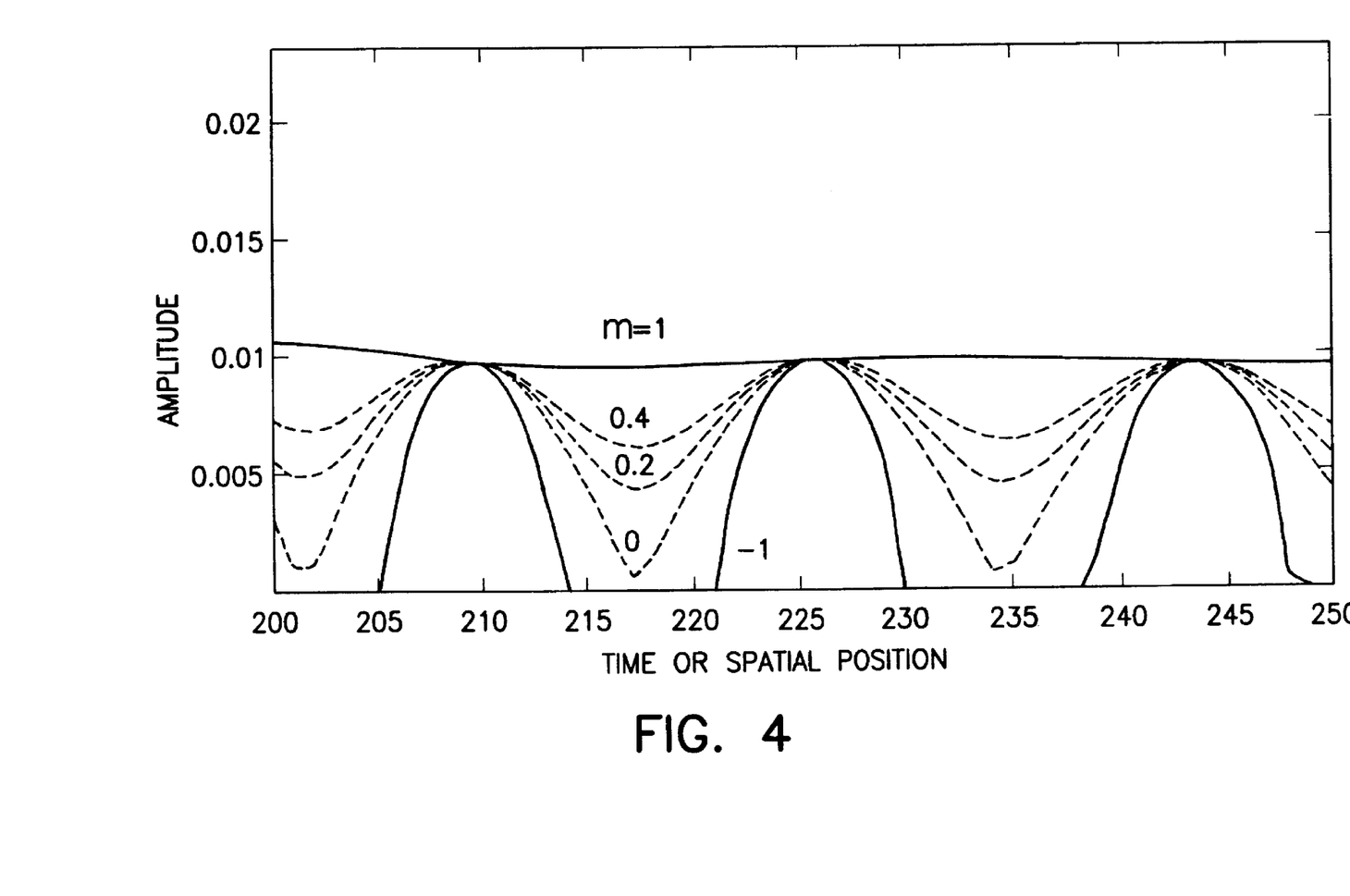
FIG. 4 is a graph of amplitude versus spatial position showing the effect of different transformation indices ($M=-1, 0, 0.2, 0.4$ and $1$) on the speckle width.

The waveform of FIG. 4 is a better illustration showing the speckle grain size for different values of M. As seen in FIG. 4, the algorithm of the present invention preserves the peak amplitude of the image signal irrespective of the value of M. Furthermore, all the spatial information in the original image is preserved and the only feature that is affected is the speckle grain size.

Different mapping curves can be used for transforming the input image with different M. Alternatively, an adaptive mapping function can be used which would not only vary M depending on the signal level intensity, but also depending on the spatial frequency contents of the image. This would be applied differently to the edges compared to the rest of the image. This would have the effect of making the thin walls appear more continuous without affecting the spatial frequency contents of the given image.

Figure 5:
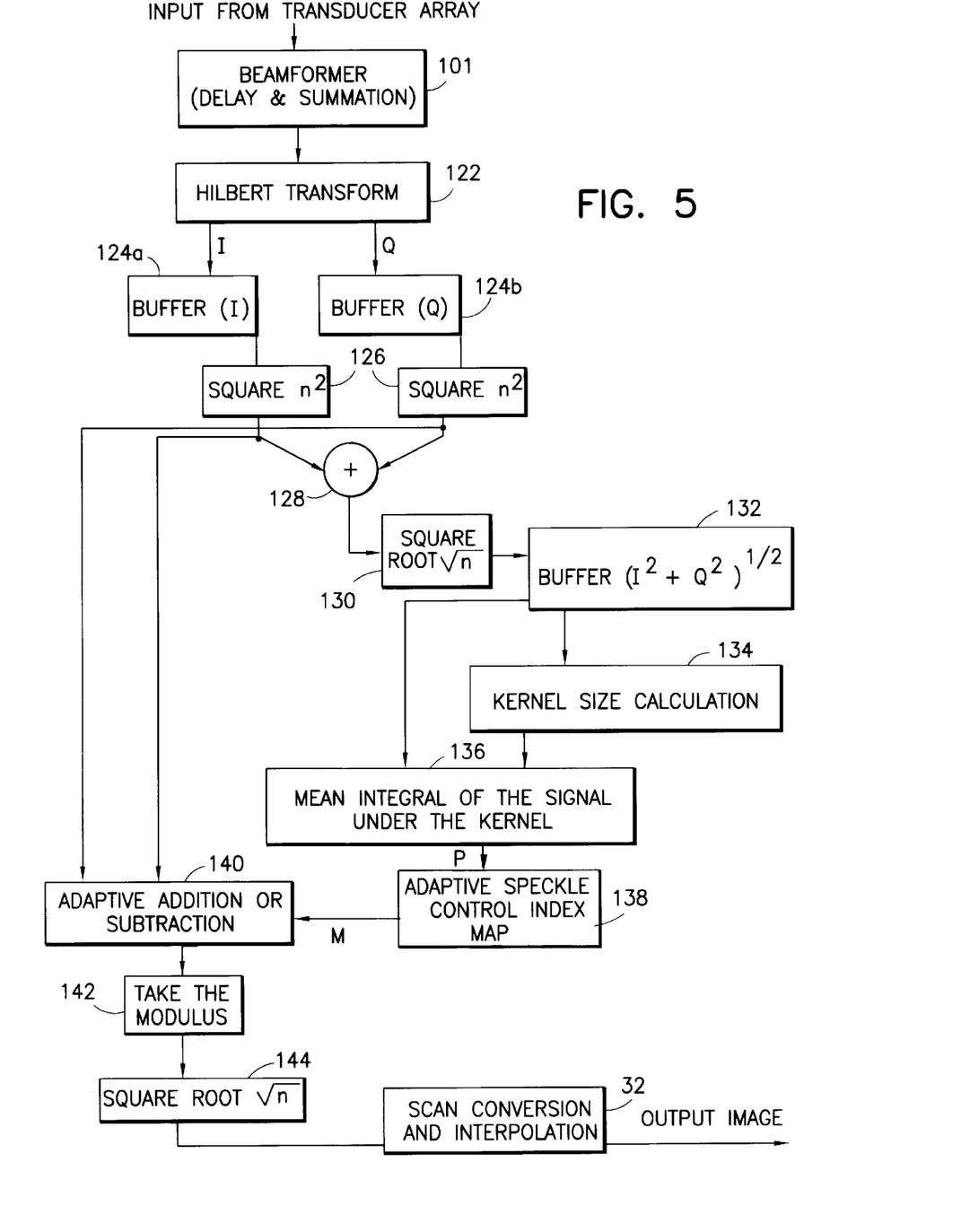
FIG. 5 is a flowchart showing the operation of a signal processor for one-dimensional adaptive speckle control using the Hilbert transformation in accordance with a preferred embodiment of the invention.

FIG. 5 is a flowchart showing the operation of signal processor for one-dimensional adaptive speckle control using the Hilbert transformation. The sequence of signal flow through the signal processing chain is as follows.

1) The input to the system is the individual signals collected by the individual elements of the transducer array.

2) The beamformer 101 simply delays the detected RF signal from the individual elements of the transducer array and sums the signals from the individual elements after the delay operation. This provides the dynamic focusing of the detected signal from the individual elements.

3) The real and imaginary components of each detected RF signal making up the A-line (an A-line is the detected single line of acoustic data after the beam formation) are generated using the Hilbert transform 122. This uses the unique property of the Hilbert transform, which can generate the quadrature component of a wideband signal.

4) After the Hilbert transformation, the real and imaginary components of the detected A-line are stored in two memory buffers 124a and 124b, which respectively store the I and Q data in the given A-line.

5) The real (I) and imaginary (Q) signals from buffers 124a and 124b are input to the signal processor 120 (see FIG. 2), where they are squared in step 126 and then added in step 128.

6) The output of step 128 is square rooted in step 130 to give the envelope of the detected signal.

7) The envelope detected signal is stored in the memory buffer 132.

8) The envelope detected signal in the memory buffer 132 is used to determine the kernel size in step 134. This kernel determines the length of the data which are integrated (or summed). The flowchart shows a one-dimensional kernel. However, the two-dimensional kernel is given in Eq. (4). The kernel size is selected such that where the amplitude of the signal is high, it would have a small kernel size. However, when the signal level is low, the kernel size is expanded. Using this technique, the small bright reflectors in the image are processed more selectively. It is possible to use a constant kernel size, but in the preferred mode of operation the kernel size is modulated depending on the signal level for the given data value. Alternatively, the kernel size can be made dependent on the spatial frequency components or edge dependent.

9) The signal under the kernel is summed by performing the mean integration (step 136) as shown in Eq. (4). The integration result is then divided by the kernel size to produce the parameter P corresponding to the mean signal level under the kernel or under the window.

10) Based on parameter P, the adaptive operator M is selected from an operation transformation map 138 stored in a look-up table. This operator can have a value in the range from +1 to −1. Some of the possible mapping functions are shown in FIGS. 6A–6D. For the given mapping function M, the operation given in Eq. (1) is performed by adding or subtracting the squares of the real and imaginary components (step 140), taking the modulus (step 142) and then calculating the square root (step 144) of the modulus in accordance with Eq. (1).

11) The processed data then undergoes scan conversion and interpolation in the scan converter 32, which stores the individual A-lines and places them adjacent to one another to form the two-dimensional image.

Thus, the existing or current systems after the beam formation perform an envelope detection and then the envelope detected A-line signals are sent onto the scan converter 32 for further processing.

Figures 6A, 6C:
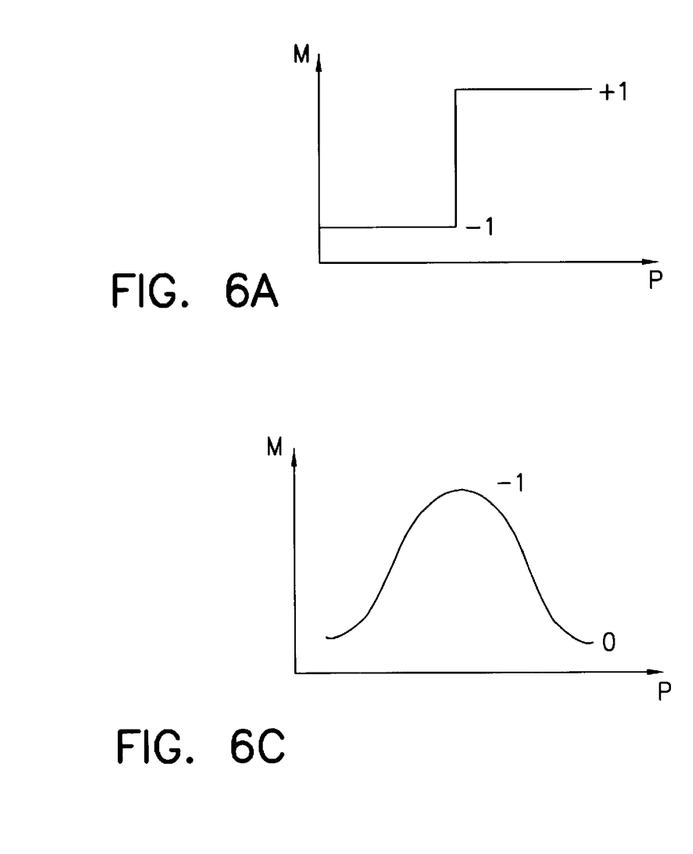
FIGS. 6A–6D are diagrams showing different possible mapping functions in accordance with the present invention.
Figure 6B:
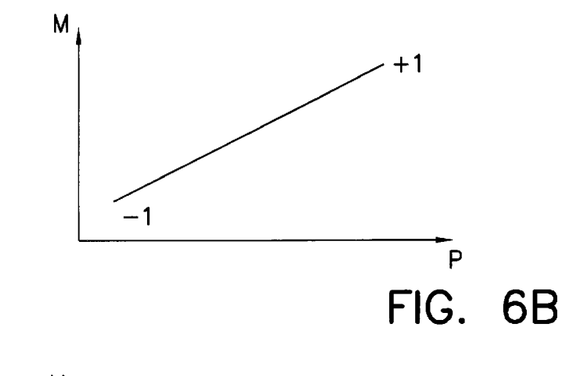
Figure 6D:
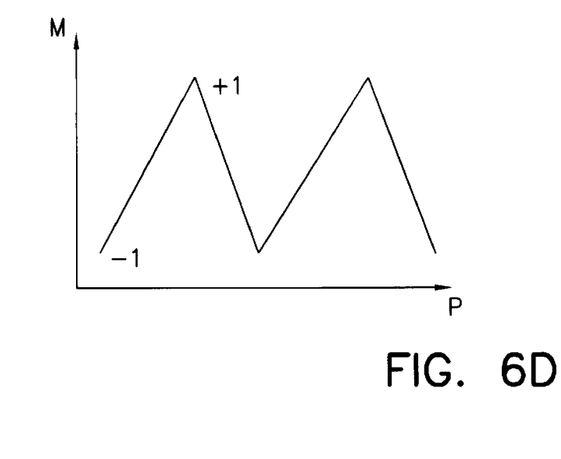

Using the different mapping functions shown in FIGS. 6A–6D, the localized speckle grains are modulated. For example, the map in FIG. 6A would make the speckle grains for the smaller echo signals smaller while the speckle grain size for the larger speckle intensity, which corresponds to stronger reflectors, is made wider. The map shown in FIG. 6A has a sharp transition point. However, the map shown in FIG. 6B has a smoother transition. Alternatively, the speckle pattern for the weak and strong reflectors could remain unchanged while the speckle pattern for the intermediate signals are modulated as shown in FIG. 6C. Another alternative mapping function is shown in FIG. 6D.

Figure 7:
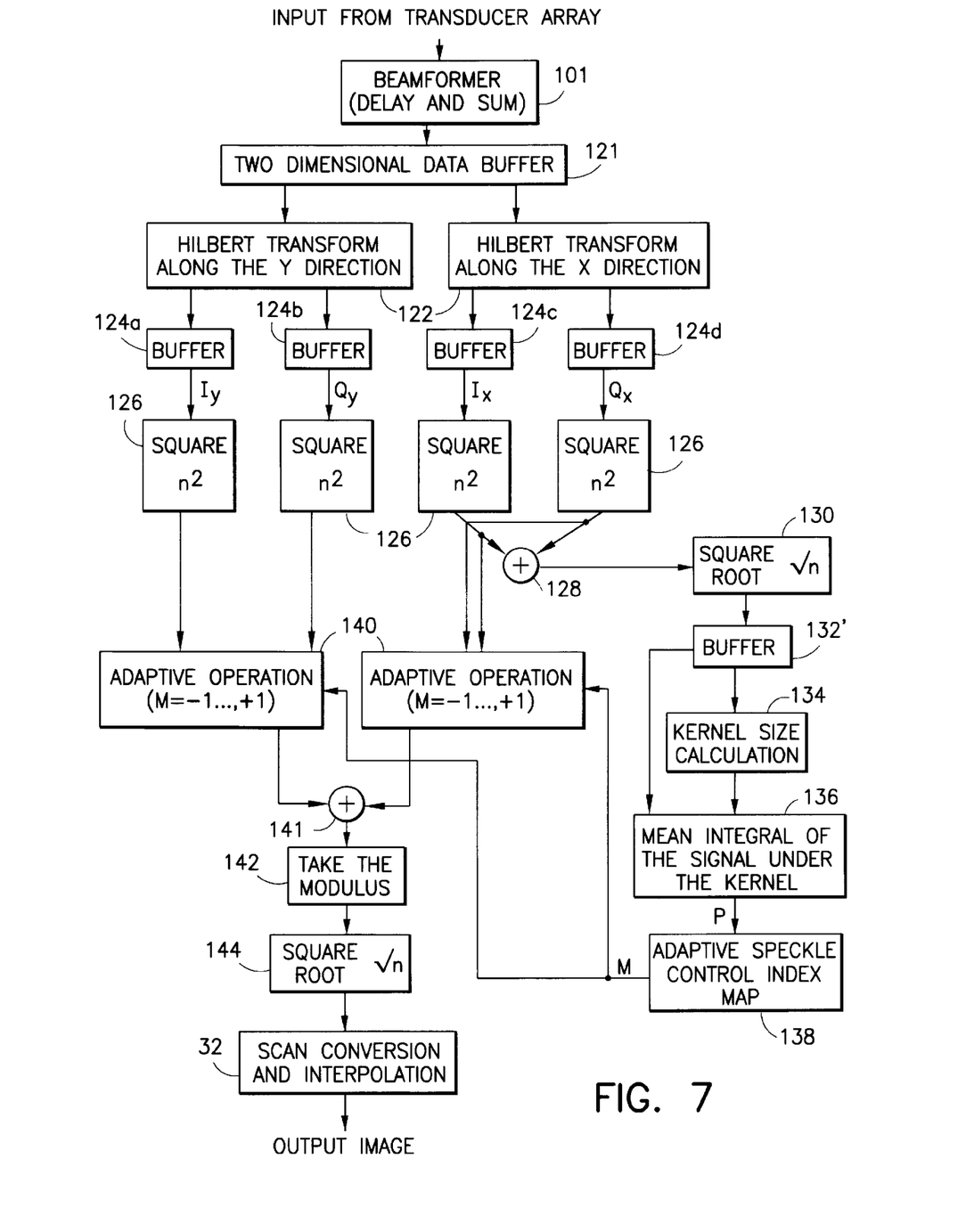
FIG. 7 is a flowchart showing the operation of a signal processor for two-dimensional adaptive speckle control using the Hilbert transformation in accordance with another preferred embodiment of the invention.
Figure 8A:
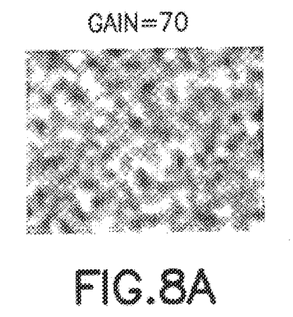
FIGS. 8A–8I are a set of typical computer-generated specular images showing the effect of variation in gain.
Figure 8B:
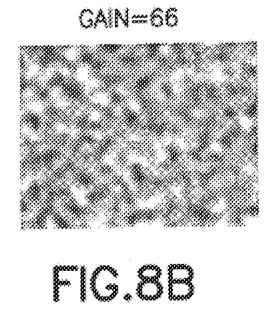
Figure 8C:
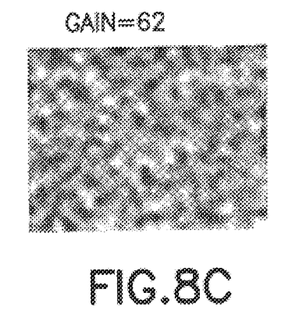
Figure 8D:
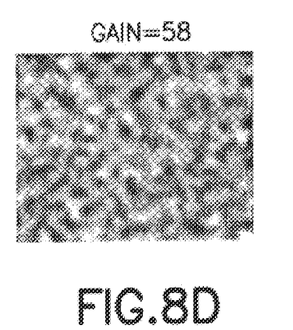
Figure 8E:
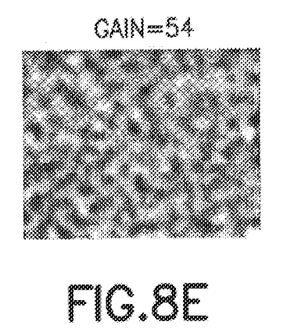
Figure 8F:
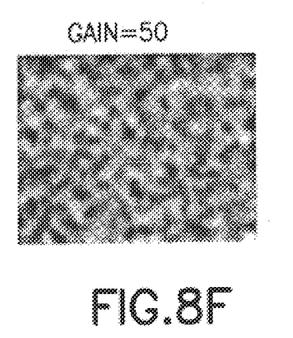
Figure 8G:
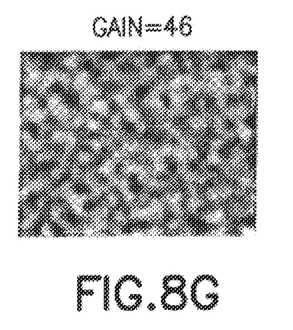
Figure 8H:
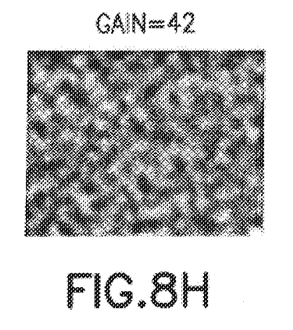
Figure 8I:
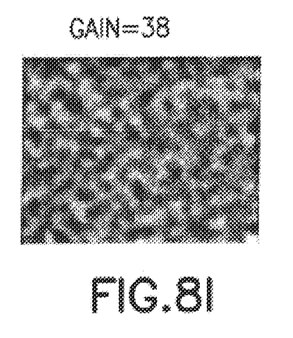
Figure 9A:
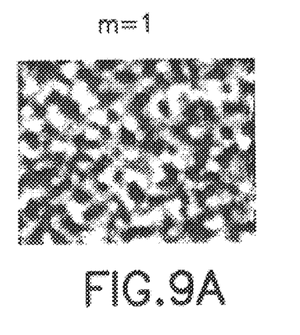
FIGS. 9A–9I are a set of typical computer-generated specular images showing the effect of variation in the Hilbert transform operator index M with constant gain and constant dynamic range.
Figure 9B:
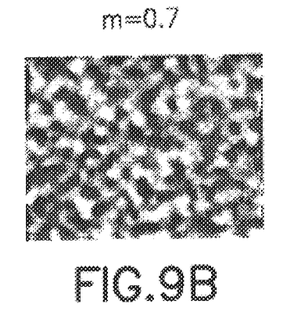
Figure 9C:
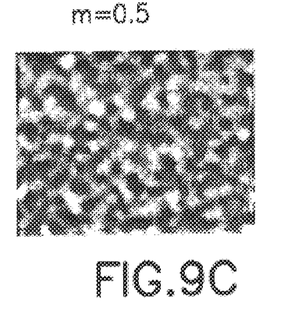
Figure 9D:
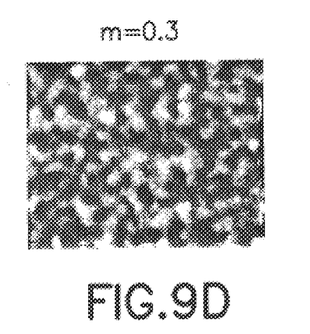
Figure 9E:
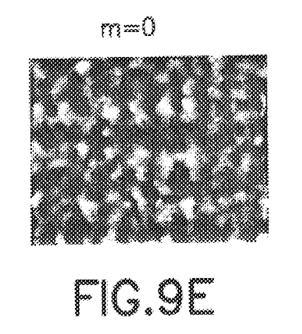
Figure 9F:
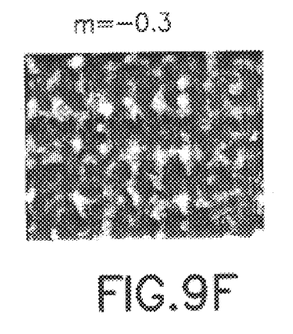
Figure 9G:
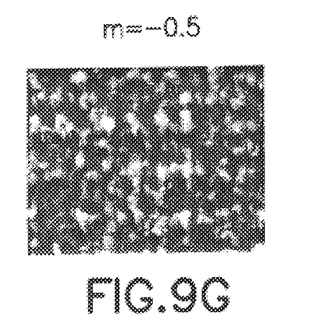
Figure 9H:
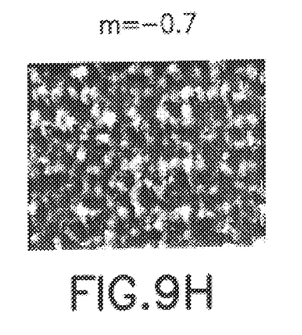
Figure 9I:
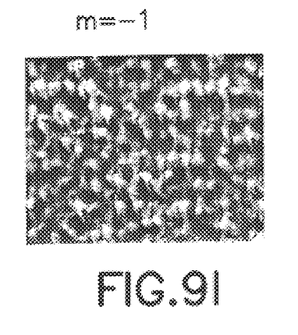

FIG. 7 is a block diagram showing the architecture of a signal processor for two-dimensional adaptive speckle control using the Hilbert transformation. The sequence of signal flow through the signal processing chain is as follows.

1) The input to the system is the signal collected from individual channels of an array transducer.

2) The beamformer 101 simply delays the detected RF signal from the individual transducer array elements and then sums the signals from the individual channels after the delay operation. This provides the dynamic focusing of the detected signal from the individual elements. Typically there are 64 to 128 channels.

3) A series of individual detected RF signal lines (i.e., A-lines) are stored in a two-dimensional data buffer 121 to form a two-dimensional map of the detected RF signals.

4) The real and the imaginary components of the detected RF signals are generated along each direction separately using the Hilbert transform 122. This uses the unique property of the Hilbert transform which can generate the quadrature component of a wideband signal. The Hilbert transform is performed separately along the x and y directions (of the map). This generates the real and the imaginary components separately along the x and y directions. Since x is the direction of propagation of ultrasound, x is the depth axis on the given two-dimensional image.

5) After the Hilbert transform along the x and y directions, the real and the imaginary components of the detected A-line signals are stored in four memory buffers 124a–124d, which store the entire data for the given A-line data sets.

6) The output of the real (I) and imaginary (Q) signals along the x direction are then squared (step 126), added (step 128) and square-rooted (step 130) to obtain the envelope detected image signal.

7) This output is the envelope detected two-dimensional image signal. This image is stored in a two-dimensional buffer 132'.

8) The envelope detected signal in the memory buffer 132' is used to determine the kernel size (step 134). This kernel determines the length of the data which are integrated (or summed). This is a two-dimensional kernel. A two-dimensional kernel is shown in Eq. (4). The kernel size is selected such that where the amplitude of the signal is high, it would have a small kernel size. However, when the signal level is low, the kernel size is expanded. Using this technique the small bright reflectors in the image are processed more selectively. It is possible to use a constant kernel size but in the preferred mode of operation the kernel size is modulated depending on the signal level for the given data value. Alternatively, the kernel size can be made dependent on the spatial frequency contents of the image under the kernel. This would be an edge-dependent operator.

9) The signal under the kernel is summed (step 136) to produce the integrated signal level. This integrated signal level is then divided by the kernel size to produce the parameter P representing the mean signal level under the kernel or under the window.

10) Based on the mean signal level under the kernel, i.e., parameter P, the adaptive speckle control index M is selected from map 138. This operator can have a value between +1 to −1. Some of the possible mapping functions are shown in FIGS. 6A–6D. For each kernel of the image, the corresponding adaptive speckle control index M is selected from the look-up table.

11) Based on the selected operator, the adaptive summation or subtraction between the squared real and the imaginary signals is performed (step 140) for each kernel in accordance with Eq. (1). This is done separately along the x and y directions. This can be a weighted sum, geometric sum or harmonic sum of two data values.

12) After the adaptive operation, the two outputs corresponding to the image information along the x and y directions are added (step 141). This can be a weighted sum, geometric sum or harmonic sum.

13) The summation of the signals from the x and y directions, after removing the sign (or taking the modulus) (step 142) are square rooted (step 144).

14) The final output is sent to the scan converter and interpolator 32 for further processing before sending the signal to the final display unit.

The effects of gain variation on specular image and the proposed adaptive Hilbert transform operator are shown in FIGS. 8A–8I and 9A–9I, respectively. These sets of images demonstrate the difference between the gain variation and the adaptive Hilbert transform operator. FIGS. 8A–8I show typical ultrasound images from a specular target. The corresponding gain is shown on the top. This shows the effect of variation in gain. For comparison, FIGS. 9A–9I are a set of images showing the effect of variation in the adaptive Hilbert transform operator index M on the image with constant gain and constant dynamic range. Going from M=1 to M=0, the individual grains of speckle start having more black area in between. The speckle pattern changes distinctly. This change in the speckle pattern is used to distinguish between different tissue types with different mean ultrasound backscatter or reflection coefficients. Going from M=0 to M=−1, the speckle patterns start to have more modulation between the individual grains of speckle. In particular, the image generated with the tissue (adaptive Hilbert transform) index of M=1 is different from M=0 and M=−1. Hence different regions can be processed according to the given transformation map.

Figure 10A:
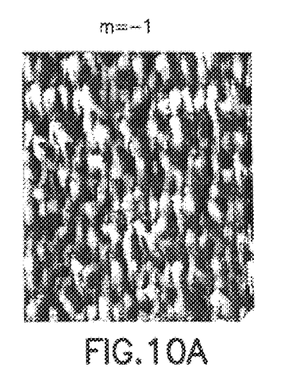
FIGS. 10A–10C are a set of typical computer-generated specular images showing different speckle patterns produced by applying different Hilbert transform operators for $M=-1, 0$ and $+1$.
Figure 10B:
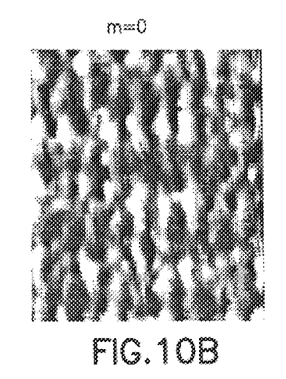
Figure 10C:
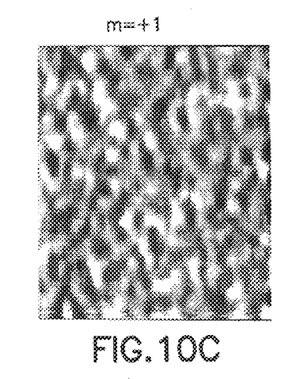

The images in FIGS. 10A–10C show the difference between different speckle patterns with different adaptive Hilbert transform operators for M=−1, 0 and 1, that is, the speckle image is changed for the same image information. By selectively applying different adaptive Hilbert transform operators to the image, different tissue regions are controlled.

Figure 11A:
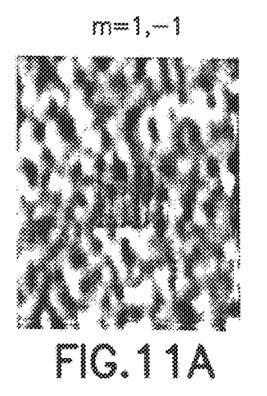
FIGS. 11A–11C are a set of computer-generated images of a region of relatively high reflection coefficient having a central portion with relatively lower reflection coefficient, the right-most image having the same adaptive Hilbert transform operator for both regions ($M=1, 1$) and the remaining two images having different adaptive Hilbert transform operators for both regions ($M=1, -1$ and $M=1, 0$).
Figure 11B:
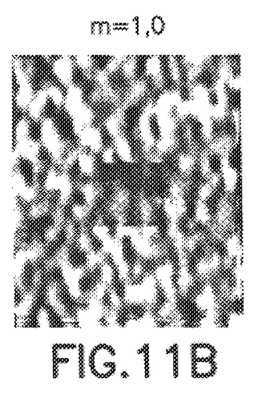
Figure 11C:
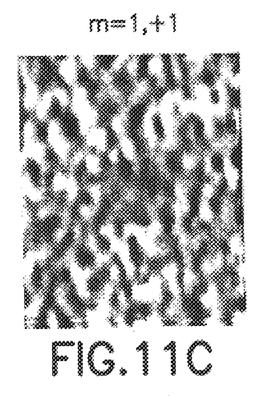

Finally, the set of images in FIGS. 11A–11C show a region with lower reflection coefficient at the middle of the image. FIG. 11C has the same adaptive Hilbert transform operator for both regions, namely, M=1, 1. The remaining two images have different adaptive Hilbert operator indexes for the central portion of the image, namely M=1, −1 and M=1, 0. This shows the difference between the conventional image and an image with adaptively selected Hilbert transform operator index. This processing makes the task of separating different reflector regions easier.

Thus, different tissue types with different acoustic reflection or backscatter coefficients can be better differentiated using the adaptive Hilbert transform operator in accordance with the present invention.

The foregoing preferred embodiments have been disclosed for the purpose of illustration. Variations and modifications will be readily apparent to those skilled in the art of baseband ultrasonic imaging systems. All such variations and modifications are intended to be encompassed by the claims set forth hereinafter.

I claim:

1. A method for adjusting speckle in an image, comprising the steps of:

acquiring an input waveform $S_{in}(x, y)$ representing an input image;

transforming said input waveform to form an in-phase component ($Re(S_{in}(x, y))$) and a quadrature phase component ($Im(S_{in}(x, y))$) of said input waveform; and computing an output waveform $S_{out}(x, y)$ representing a speckle-modulated region of said input image in accordance with the following equation:

$$S_{out}(x,y)=|\{(Re(S_{in}(x,y))^2+M(Im(S_{in}(x,y))^2\}|^{0.5}$$

wherein M is an adaptive speckle control index having a value in a range $-1 \leq M < 1$.

2. The method as defined in claim 1, wherein the quadrature phase component is computed using the Hilbert transform.

3. The method as defined in claim 1, further comprising the step of concurrently displaying said speckle-modulated region of said input image in conjunction with a non-speckle-adjusted region of said input image.

4. The method as defined in claim 3, further comprising the steps of scan converting and interpolating said output waveform prior to displaying.

5. The method as defined in claim 1, wherein said computing step comprises the steps of:

computing a quantity $[(Re(S_{in}(x, y))^2+(Im(S_{in}(x, y))^2]^{1/2}$ for each sample of said input waveform;

determining a size of said kernel in dependence on said computed quantity;

integrating said computed quantity over said kernel;

dividing the integrated quantity by the area of the kernel, resulting in a mean integrated value; and selecting a value for said adaptive speckle control index M by inputting said mean integrated value into a mapping of M values.

6. The method as defined in claim 5, wherein the product of kernel area and said input sample data is constant.

7. The method as defined in claim 5, wherein the kernel size is proportional to the localized spatial frequency contents of the input image waveform.

8. The method as defined in claim 1, wherein said acquiring step comprises the step of beamforming.

9. A method for ultrasound imaging of an object, comprising the steps of:

transmitting an ultrasound beams along a scan line into an object to be imaged;

forming an acoustic data signal representing the amplitude of a net ultrasound beam reflected by said object from a range point along said scan line, said acoustic data signal beamforming step being performed for each of a multiplicity of range points along said scan line;

transforming each acoustic data signal to form an in-phase component and a quadrature phase component thereof;

for at least one of said transformed acoustic data signals, generating adaptive acoustic data signals which represent the square root of the absolute value of a sum of the square of said in-phase component plus the product of an adaptive speckle control index times the square of said quadrature phase components, wherein said adaptive speckle control index has a value $\geq -1 < +1$; and displaying a specular image of said adaptive acoustic data signals.

10. The method as defined in claim 9, wherein the quadrature phase component is computed using the Hilbert transform.

11. The method as defined in claim 9, further comprising the steps of:

computing an amplitude of an envelope of said in-phase component and said quadrature component for each of said acoustic data signals;

determining a size of a kernel in dependence on said computed envelope amplitude;

integrating said computed envelope amplitude over said kernel;

adjusting the kernel size to have a constant integrated value, but different mean integrated value; and selecting a value for said adaptive speckle control index by inputting the result of said integrating step into a mapping of adaptive speckle control index values.

12. An apparatus for adjusting speckle in an image, comprising:

a beamformer for acquiring an input waveform $S_{in}(x, y)$ representing an input image;

means for transforming said input waveform to form an in-phase component ($Re(S_{in}(x, y))$) and a quadrature phase component ($Im(S_{in}(x, y))$) of said input waveform;

processing means for computing an output waveform $S_{out}(x, y)$ representing a speckle-modulated region of said input image in accordance with the following equation:

$$S_{out}(x,y)=|\{(Re(S_{in}(x,y))^2+M(Im(S_{in}(x,y))^2\}|^{0.5}$$

wherein M is an adaptive speckle control index having a value in a range $-1 \leq M < 1$; and means for displaying said speckle-modulated region of said input image in conjunction with a non-speckle-adjusted region of said input image.

13. The apparatus as defined in claim 12, wherein the quadrature phase component is computed using the Hilbert transform.

14. The apparatus as defined in claim 12, further comprising a scan converter and an interpolator for scan converting and interpolating said output waveform prior to display.

15. The apparatus as defined in claim 12, wherein said processing means comprise:

means for computing a quantity $[.(Re(S_{in}(x, y))^2+(Im(S_{in}(x, y))^2]^{1/2}$ for each sample of said input waveform;

means for determining a size of said kernel in dependence on said computed quantity;

means for integrating said computed quantity over said kernel;

means for storing a mapping of M values; and means for selecting a value for said adaptive speckle control index M by inputting the result of said integrating step into said mapping of M values.

16. The apparatus as defined in claim 15, wherein the product of kernel area and said input sample data is constant.

17. The apparatus as defined in claim 15, wherein the kernel size is proportional to the localized spatial frequency contents of the input image waveform.

* * * * *